(12) United States Patent
Tabuchi et al.

(10) Patent No.: US 7,307,165 B2
(45) Date of Patent: Dec. 11, 2007

(54) PROCESS FOR PRODUCTING IMIDAZO[1,2-B]PYRIDAZINE DERIVATIVE

(75) Inventors: Takanori Tabuchi, Osaka (JP); Tetsuhiro Yamamoto, Nishinomiya (JP); Takeshi Kajiwara, Ibaraki (JP)

(73) Assignee: Sumitomo Chemical Takeda Agro Company, Limited, Tokyo (JP)

( * ) Notice: Subject to any disclaimer, the term of this patent is extended or adjusted under 35 U.S.C. 154(b) by 435 days.

(21) Appl. No.: 10/522,798

(22) PCT Filed: Jul. 16, 2003

(86) PCT No.: PCT/JP03/09003

§ 371 (c)(1),
(2), (4) Date: Feb. 28, 2005

(87) PCT Pub. No.: WO2004/011466

PCT Pub. Date: Feb. 5, 2004

(65) Prior Publication Data

US 2005/0171108 A1    Aug. 4, 2005

(30) Foreign Application Priority Data

Jul. 29, 2002 (JP) .............................. 2002-219786
Mar. 26, 2003 (JP) .............................. 2003-085617

(51) Int. Cl.
    *C07D 487/04* (2006.01)
(52) U.S. Cl. .................................... 544/236
(58) Field of Classification Search ................ 544/236
    See application file for complete search history.

(56) References Cited

U.S. PATENT DOCUMENTS 6,627,630 B1 * 9/2003 Kawano et al. ............. 514/248

FOREIGN PATENT DOCUMENTS

JP    1-316379    12/1989
WO    00/23450    4/2000
WO    03/061388   7/2003

OTHER PUBLICATIONS

Gyoten, et al., Chem Pharm. Buss., 51(2), 122-133 (Feb. 2003).*
Ishikawa, et al., J. Antibio., vol. 54, No. s, Mar. 2001.*
K. Tamao et al., "Nickel-Phosphine Complex-Catalyzed Grignard Coupling. I. Cross-Coupling of Alkyl, Aryl, and Alkenyl Grignard Reagents with Aryl and Alkenyl Halides: General Scope and Limitations", vol. 49, No. 7, pp. 1958-1969, Jul. 1979.
A. E. Mourad et al., "Methyl imidazo [1,2-b] pyridazine-2-carbamates and related compounds as potential antifilarial agents", J. Heterocyclic Chem., vol. 29, pp. 1583-1592, 1992.
A. Pollak et al., "Synthesys of pyridazine derivatives", Tetrahedron, vol. 24, No. 6, pp. 2623-2629, 1968.
T. Ishikawa et al., "Studies on anti-MRSA parenteral cephalosporins", The Journal of Antibiotics, vol. 54, No. 3, pp. 257-277, 2001.
K. Satoh et al., "Reactivity of imidazo [1,2-b], pyridazine 1-oxide", Heterocycles, vol. 10, pp. 269-276, 1978.

* cited by examiner

*Primary Examiner*—Mark L. Berch
*Assistant Examiner*—Cecilia M Jaisle
(74) *Attorney, Agent, or Firm*—Wenderoth, Lind & Ponack, L.L.P.

(57) ABSTRACT

A process for easily and inexpensively producing an imidazo [1,2-b]pyridazin-3-ylsulfonamide derivative which has a substituent bonded to the 6-position carbon atom and is represented by the formula (II):

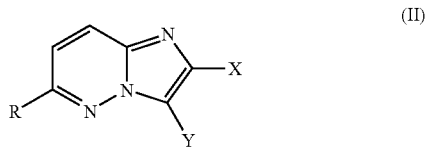

(II)

(wherein R represents lower alkyl, lower cycloalkyl optionally substituted by lower alkyl, lower alkenyl, or lower alkynyl), the process comprising reacting an imidazo[1,2-b]pyridazine compound represented by the formula (I):

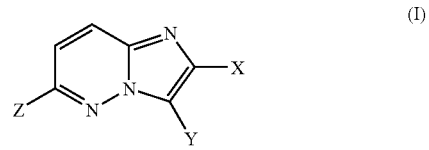

(I)

(wherein X represents halogeno or lower alkyl optionally substituted by halogeno; Y represents hydrogen or $SO_2N{=}CH{-}NR^1R^2$; and Z represents halogeno or $OSO_2R^3$) with an organometallic compound in the presence of a transition metal catalyst. The derivative is useful as an intermediate for herbicides.

12 Claims, No Drawings

PROCESS FOR PRODUCTING IMIDAZO[1,2-B]PYRIDAZINE DERIVATIVE

TECHNICAL FIELD

This invention relates to a novel process for producing an imidazo[1,2-b]pyridazine derivative having a substituent bonded to the 6-position carbon atom which is used for producing a sulfonylurea compound having a fused heterocyclic ring useful as a herbicide, and an intermediate thereof.

BACKGROUND ART

Sulfonylurea compounds having a fused heterocyclic ring are known as a herbicide having a high herbicidal activity and high safety for crops (e.g., see JP-B H05-36439 and JP-A H01-139582). Among them, a sulfonylurea compound having imidazo[1,2-b]pyridazine ring as a fused heterocyclic ring is one of compound groups having a high activity, especially the present inventors found out that a compound having a substituent bonded to the 6-position carbon atom of imidazo[1,2-b]pyridazine ring has a high herbicidal activity against weeds resistant to conventional sulfonylurea herbicides, and filed a patent application (JP Application No. 2003-6756). As a reaction for introducing a substituent at the 6-position carbon atom of imidazo[1,2-b]pyridazine ring, Journal of Antibiotics, 54 (3), 257-277, 2001; Synthesis, (4), 595-600, 2001; JP-A H05-271233; JP-A H06-116272; JP-A H11-310581; JP-A H11-310582; JP-A 2000-198735; JP-A 2001-199889 and the like are known.

The object of this invention is to provide a process for easily and inexpensively producing an imidazo[1,2-b]pyridazin-3-ylsulfonamide derivative having a substituent bonded to the 6-position carbon atom which is useful as a synthetic intermediate for herbicides.

DISCLOSURE OF INVENTION

To solve the above-mentioned problem, the present inventors made extensive study to find out an easy and inexpensive production process of imidazo[1,2-b]pyridazin-3-ylsulfonamide compound having a substituent bonded to the 6-position carbon atom over the years, and as a result, found out that an imidazo[1,2-b]pyridazine derivative having a substituent bonded to the 6-position carbon atom can be obtained unexpectedly with a convenient operation and in good yield by reacting an imidazo[1,2-b]pyridazine derivative having a leaving group at the 6-position with an organometallic compound under the presence of transition metal catalyst. After further studying extensively based on these knowledge, this invention was thereby completed.

That is, this invention relates to:

(1) A process for producing a compound represented by the formula (II):

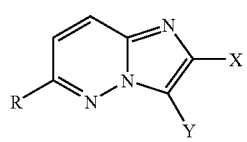

(II)

wherein X represents a halogen atom or an optionally halogenated lower alkyl group, Y represents a hydrogen atom or $SO_2N=CH-NR^1R^2$ (wherein $R^1$ and $R^2$ represent each lower alkyl group, or $R^1$ and $R^2$ may be combined together with the adjacent nitrogen atom to form a heterocyclic ring), and R represents a lower alkyl group, lower cycloalkyl group which may be substituted with lower alkyl, lower alkenyl group or lower alkynyl group (also referred to hereinafter as Compound (II)), which comprises reacting an imidazo[1,2-b]pyridazine compound represented by the formula (I):

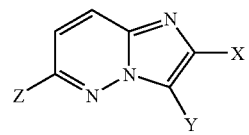

(I)

wherein X and Y are as defined above, and Z represents a halogen atom or $OSO_2R^3$ (wherein $R^3$ represents an optionally fluorinated lower alkyl group or phenyl group which may be substituted with lower alkyl) (also referred to hereinafter as Compound (I)), with one or more compounds selected from the organometallic compounds represented by the formula:

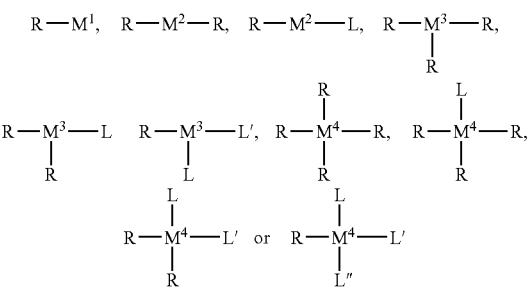

wherein R is as defined above, and $M^1$ represents an univalent metal, $M^2$ represents a divalent metal, $M^3$ represents a trivalent metal and $M^4$ represents a tetravalent metal, and L, L' and L" are the same or different and represent an anion, under the presence of transition metal catalyst, (2) The process according to the above-mentioned (1), wherein the metal of the transition metal catalyst is palladium, nickel or iron, (3) The process according to the above-mentioned (1), wherein the metal of the transition metal catalyst is nickel, (4) The process according to the above-mentioned (1), wherein the metal of the organometallic compound is magnesium or zinc, (5) The process according to the above-mentioned (1), wherein R is a lower alkyl group or lower cycloalkyl group which may be substituted with lower alkyl, (6) The process according to the above-mentioned (1), wherein X and Z are a chlorine atom, (7) The process according to the above-mentioned (1), wherein Y is a hydrogen atom and R is a lower alkyl group, (8) The process according to the above-mentioned (3), wherein the metal of the organometallic compound is magnesium or zinc, (9) The process according to the above-mentioned (8), wherein the organometallic compound is a lower alkylmagnesium halide or a lower-alkylzinc halide,

(10) The process according to the above-mentioned (9), wherein the organometallic compound is a propylmagnesium halide or propylzinc halide and the nickel catalyst is [1,3-bis(diphenylphosphino)propane]nickel (II) dichloride or bis(triphenylphosphine)nickel (II) dichloride,

(11) A process for producing a sulfonamide compound represented by the formula (III):

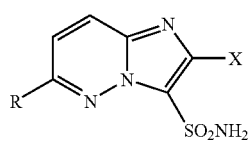

wherein X represents a halogen atom or an optionally halogenated lower alkyl group and R represents a lower alkyl group, lower cycloalkyl group which may be substituted with lower alkyl, lower alkenyl group or lower alkynyl group (also referred to hereinafter as Compound (III)), which comprises sulfonating with chlorosulfonic acid a compound represented by the formula (IIa):

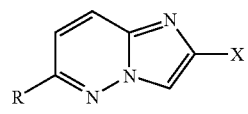

wherein X and R are as defined above (also referred to hereinafter as Compound (IIa)), which is obtained by reacting an imidazo[1,2-b]pyridazine compound represented by the formula (Ia):

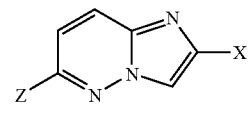

wherein X is as defined above, and Z represents a halogen atom or $OSO_2R^3$ (wherein $R^3$ represents an optionally fluorinated lower alkyl group or phenyl group which may be substituted with lower alkyl) (also referred to hereinafter as Compound (Ia)), with one or more compounds selected from the organometallic compounds represented by the formula:

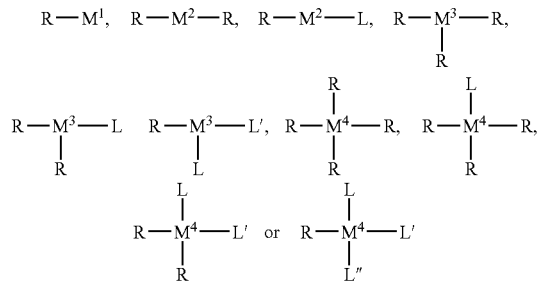

wherein R is as defined above, and $M^1$ represents an univalent metal, $M^2$ represents a divalent metal, $M^3$ represents a trivalent metal and $M^4$ represents a tetravalent metal, and L, L' and L" are the same or different and represent an anion, under the presence of transition metal catalyst, followed by converting to a sulfonyl chloride with phosphorus oxychloride, then reacting with ammonia, and

(12) A process for producing a sulfonamide compound represented by the formula (III):

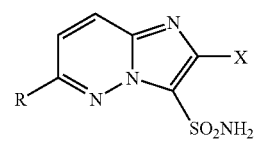

wherein X represents a halogen atom or an optionally halogenated lower alkyl group and R represents a lower alkyl group, lower cycloalkyl group which may be substituted with lower alkyl, lower alkenyl group or lower alkynyl group, which comprises hydrolyzing under the presence of acid or alkali a compound represented by the formula (IIb):

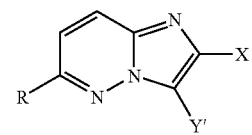

wherein X and R are as defined above and Y' represents $SO_2N=CH-NR^1R^2$ (wherein $R^1$ and $R^2$ represent each lower alkyl group, or $R^1$ and $R^2$ may be combined together with the adjacent nitrogen atom to form a heterocyclic ring) (also referred to hereinafter as Compound (IIb)), which is obtained by reacting an imidazo[1,2-b]pyridazine compound represented by the formula (Ib):

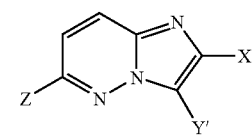

wherein X and Y' are as defined above, and Z represents a halogen atom or $OSO_2R^3$ (wherein $R^3$ represents an optionally fluorinated lower alkyl group or phenyl group which may be substituted with lower alkyl) (also referred to hereinafter as Compound (Ib)), with one or more compounds selected from the organometallic compounds represented by the formula:

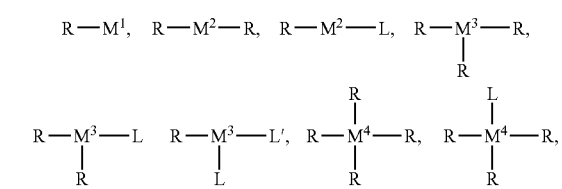

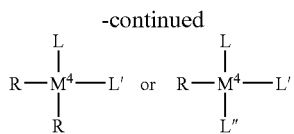

wherein R is as defined above, and $M^1$ represents an univalent metal, $M^2$ represents a divalent metal, $M^3$ represents a trivalent metal and $M^4$ represents a tetravalent metal, and L, L' and L" are the same or different and represent an anion, under the presence of transition metal catalyst.

MODE FOR CARRYING OUT THE INVENTION

The present invention will be described in detail below.

Given the term "lower" in the lower alkyl group, lower alkenyl group, lower alkynyl group etc. in this specification, these alkyl group and the like are meant to be composed of 1 or 2 to 6 carbon atoms, preferably 1 or 2 to 4 carbon atoms. For example, a linear or branched $C_{1-6}$ alkyl group, $C_{2-6}$ alkenyl group and $C_{2-6}$ alkynyl group are exemplified. In addition, the "lower cycloalkyl group" means $C_{3-7}$ cycloalkyl group having 3 to 7 carbon atoms.

In the above-mentioned formulas (I), (Ia) and (Ib), X represents a halogen atom or an optionally halogenated lower alkyl group, and the "halogen atom" in "halogen atom" and "optionally halogenated lower alkyl group" includes, for example, fluorine, chlorine, bromine, iodine etc. Examples of the "lower alkyl group" in "optionally halogenated lower alkyl group" include $C_{1-6}$ alkyl group such as methyl, ethyl, propyl, isopropyl, butyl, isobutyl, s-butyl, t-butyl etc. Examples of preferable substituent as X include fluorine, chlorine, methyl, ethyl, trifluoromethyl and the like.

When $R^1$ and $R^2$ of $SO_2N=CH-NR^1R^2$ for Y and Y' in the above formulas (I) and (Ib) represent independently a lower alkyl group, the "lower alkyl group" includes, for example, $C_{1-6}$ alkyl group such as methyl, ethyl, propyl, isopropyl, butyl, isobutyl, s-butyl, t-butyl etc., and the "heterocyclic ring" in case that "$R^1$ and $R^2$ are combined together with the adjacent nitrogen atom to form a heterocyclic ring" includes, for example, a 3- to 10-membered (preferably, 3- to 6-membered) nitrogen-containing heterocyclic ring such as azetidine ring, pyrrolidine ring, piperidine ring, and the like.

In the above-mentioned formulas (I), (Ia) and (Ib), the "halogen atom" for Z includes, for example, fluorine, chlorine, bromine, iodine etc. The "lower alkyl group" in the "optionally fluorinated lower alkyl group" for $R^3$ of "$OSO_2R^3$" includes, for example, $C_{1-6}$ alkyl group such as methyl, ethyl, propyl, isopropyl, butyl, isobutyl, s-butyl, t-butyl etc. The "lower alkyl group" of the "phenyl group which may be substituted with lower alkyl" includes, for example, $C_{1-6}$ alkyl group such as methyl, ethyl, propyl, isopropyl, butyl, isobutyl, s-butyl, t-butyl etc. Examples of preferable substituent as Z include a halogen atom, in particular, chlorine and bromine are preferred.

In the organometallic compounds represented by the formula:

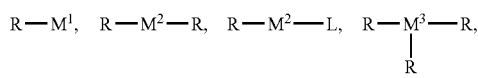

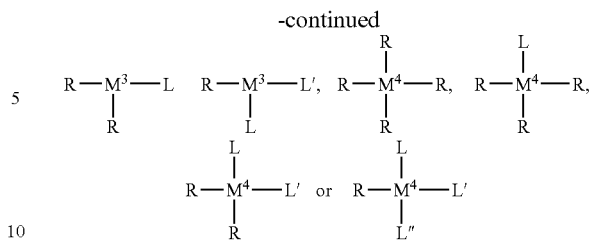

and formulas (II), (IIa) and (IIb), examples of the "lower alkyl group" in the "lower alkyl group" and "lower cycloalkyl group which may be substituted with lower alkyl" for R include $C_{1-6}$ alkyl group such as methyl, ethyl, propyl, isopropyl, butyl, isobutyl, s-butyl, t-butyl etc. Examples of the "lower cycloalkyl group" in the "lower cycloalkyl group which may be substituted with lower alkyl" include $C_{3-7}$ cycloalkyl such as cyclopropyl, cyclobutyl, cyclopentyl, etc. Examples of the "lower alkenyl group" include $C_{2-6}$ alkenyl such as ethenyl, 1-propenyl, 2-propenyl, 1-butenyl, 2-butenyl, 3-butenyl, etc., and examples of the "lower alkynyl group" include $C_{2-6}$ alkynyl such as ethynyl, 1-propynyl, 2-propynyl, 2-butynyl etc. The preferred substituent as R includes ethyl, propyl, isopropyl and cyclopropyl.

As $M^1$ which represents an univalent metal in the above-mentioned organometallic compounds, lithium, sodium, potassium, rubidium, univalent copper, and the like are exemplified. $M^2$ which represents a divalent metal include, for example, magnesium, calcium, strontium, barium, zinc, cadmium, mercury, divalent copper, divalent lanthanoid metal and the like. $M^3$ which represents a trivalent metal include, for example, boron, aluminum, trivalent lanthanoid metal and the like. $M^4$ which represents a tetravalent metal include, for example, silicon, germanium, tin, lead, titanium, zirconium, cerium and the like. Preferred metal is an univalent or divalent metal, and in particular, magnesium or zinc is preferred.

The anions represented by L, L' or L" in the above-mentioned organometallic compounds are the same or different and include, for example, a halogen such as fluorine, chlorine, bromine, iodine etc., $C_{1-6}$ alkoxy group such as methoxy, ethoxy, propoxy etc., phenoxy group, $C_{1-6}$ alkyl group such as methyl, ethyl, propyl, isopropyl, butyl etc., carboxylic acid anion such as acetate, trifluoroacetate, benzoate etc., phenyl group, cyano group, hydroxy group and the like, or two of L, L' or L" may be combined together to form a dialkoxide of diol such as ethylene glycol and catechol. Preferred is a halogen.

Preferable examples of the organometallic compound include organic alkalimetallic compound, organic alkaline earth metallic compound, organozinc compound, organocupric compound, organosilicon compound and organolead compound, and in particular, preferred are organomagnesium halide and organozinc halide.

The organometallic compound is usually commercially available or prepared from a halide such as alkyl halide, cycloalkyl halide, alkenyl halide, alkynyl halide, etc. and a metal simple substance, or it can be obtained by a metal exchange reaction of easily available organometallic compound and other metal salt. Examples thereof include a preparation of organozinc compound by a reaction of organolithium compound or organomagnesium compound with zinc chloride, a preparation of organotitanium compound by a reaction of organolithium compound or organomagnesium compound with titanium chloride, a preparation of organocerium compound by a reaction of organolithium compound or organomagnesium compound with cerium chloride, a preparation of organocopper compound by a reaction of organolithium compound or organomagnesium compound with copper chloride, and the like.

Furthermore, the organometallic compound can be used with generating it from a halide such as alkyl halide, cycloalkyl halide, alkenyl halide, alkynyl halide, etc. and a metal simple substance in the system of coupling reaction with imidazo[1,2-b]pyridazines.

Examples of the transition metal catalyst include a transition metal simple substance, a catalyst wherein transition metal is fixed on a carrier, a transition metal complex, a polymerized transition metal, a transition metal complex which is fixed in a microcapsule, and the like. Examples of the transition metal include titanium, vanadium, chromium, manganese, iron, cobalt, nickel, cupper, zirconium, niobium, molybdenum, ruthenium, rhodium, palladium, silver, hafnium, tantalum, tungsten, rhenium, osmium, iridium, platinum, gold etc., and preferred is palladium, nickel or iron, and in particular, nickel is preferred.

In the case of complex, examples of ligand include a halogen anion such as fluorine anion, chlorine anion, bromine anion, iodine anion, cyano anion, alkoxy anion such as methoxy, ethoxy, isopropoxy etc., carboxylic acid anion such as acetate anion, trifluoroacetate anion etc., sulfonic acid anion such as methanesulfonate, trifluoromethanesulfonate, p-toluenesulfonate etc., amines such as ammonia, methylamine, ethylamine, dimethylamine, ethylenediamine, triethylamine, aniline, N,N-dimethylaniline etc., pyridine, 2,2'-bipyridyl, imidazole, alkoxides of aminoalcohol such as ethanolamine, propanolamine etc., phosphines such as tributylphosphine, tricyclohexylphosphine, triphenylphosphine, 1,2-bis(diphenylphosphino)ethane, 1,3-bis(diphenylphosphino)propane, 1,4-bis(diphenylphosphino)butane etc., aminoalkylphosphines such as 2-(dimethylamino)ethyldiphenylphosphine etc., alkoxides of hydroxyalkylphosphine such as diphenyl(2-hydroxyethyl)phosphine etc., carbon monoxide, ethylene, butadiene, cyclopentadienyl anion, 1,5-cyclooctadiene, acetonitrile, benzonitrile, acetylacetonate anion, dibenzalacetone, and the like. The transition metal complex is composed of same or different 1 to 6 ligands selected from the above-mentioned ligands.

The transition metal complex is preferably a palladium or nickel complex containing phosphines as a ligand such as bis(triphenylphosphine)nickel(II) dichloride, bis(triphenylphosphine)nickel(II) dibromide, [1,3-bis(diphenylphosphino)propane]nickel(II) dichloride, [1,3-bis(diphenylphosphino)propane]nickel(II) dibromide, bis(triphenylphosphine)palladium(II) dichloride, bis(triphenylphosphine)palladium(II) dibromide, [1,3-bis(diphenylphosphino)propane]palladium(II) dichloride, [1,3-bis(diphenylphosphino)propane]palladium(II) dibromide and tetrakis(triphenylphosphine)palladium, or an iron compound such as iron(II) chloride, iron(III) chloride or iron(III) acetylacetonate, and particularly preferred are bis(triphenylphosphine)nickel(II) dichloride, [1,2-bis(diphenylphosphino)ethane]nickel(II) dichloride and [1,3-bis(diphenylphosphino)propane]nickel(II) dichloride.

The transition metal complex is usually commercially available or prepared by a known method, or the transition metal complex can be used with generating it in the coupling reaction system by adding a transition metal salt and a ligand separately. Examples thereof include a combination of nickel chloride and triphenylphosphine, a combination of nickel bromide and triphenylphosphine, a combination of nickel acetate and triphenylphosphine, a combination of palladium chloride and triphenylphosphine, a combination of palladium bromide and triphenylphosphine, a combination of palladium acetate and triphenylphosphine, a combination of nickel chloride and 1,2-bis(diphenylphosphino)ethane, a combination of nickel bromide and 1,2-bis(diphenylphosphino)ethane, a combination of nickel acetate and 1,2-bis(diphenylphosphino)ethane, a combination of palladium chloride and 1,2-bis(diphenylphosphino)ethane, a combination of palladium bromide and 1,2-bis(diphenylphosphino)ethane, a combination of palladium acetate and 1,2-bis(diphenylphosphino)ethane, a combination of nickel chloride and 1,3-bis(diphenylphosphino)propane, a combination of nickel bromide and 1,3-bis(diphenylphosphino)propane, a combination of nickel acetate and 1,3-bis(diphenylphosphino)propane, a combination of palladium chloride and 1,3-bis(diphenylphosphino)propane, a combination of palladium bromide and 1,3-bis(diphenylphosphino)propane, a combination of palladium acetate and 1,3-bis(diphenylphosphino)propane, and the like.

The reaction in the production of compound (II) from compound (I) is carried out without solvent or with making a dilution in solvent. Examples of the reaction solvent include hydrocarbon solvents such as petroleum ether, pentane, hexane, cyclohexane, benzene, toluene, xylene etc., halogenated hydrocarbon solvents such as dichloromethane, 1,2-dichloroethane, chloroform, carbon tetrachloride, trichloroethane, trichloroethylene, tetrachloroethane, chlorobenzene, etc., ether solvents such as diethyl ether, methyl t-butyl ether, tetrahydrofuran (abbreviation: THF), 1,4-dioxane, dimethoxyethane (abbreviation: DME), diethylene glycol dimethyl ether, etc., ketone solvents such as acetone, methyl ethyl ketone, 2-pentanone, 3-pentanone, cyclohexanone, etc., ester solvents such as ethyl acetate, butyl acetate, etc., amide solvents such as N,N-dimethylformamide (abbreviation: DMF), N,N-dimethylacetamide, N-methylpyrrolidone, etc., nitrile solvents such as acetonitrile, propionitrile, etc., solvents containing sulfur such as dimethyl sulfoxide, dimethyl sulfone, solfolane, carbon disulfide, etc., nitro compound solvents such as nitromethane, nitrobenzene, etc., protic solvents such as water, methanol, ethanol, propanol, isopropanol, t-butanol, ethylene glycol, phenol, acetic acid, etc. As a preferable solvent, hydrocarbon solvents or ether solvents are exemplified. These solvents are usually used alone, or may be used with mixing in an appropriate ratio.

The reaction temperature is −100° C. to 300° C., preferably −50° C. to 100° C., and more preferably −20° C. to 50° C.

The reaction time is 10 seconds to 500 hours, preferably 1 minute to 48 hours, and more preferably 10 minutes to 24 hours.

The ratio of the organometallic compound used to compound (I) is 0.5 to 10 equivalents, preferably 0.8 to 3.0 equivalents, and particularly preferably 1.0 to 1.5 equivalents.

The ratio of the transition metal catalyst used to compound (I) is 0.000001 to 10 equivalents, preferably 0.00001 to 1 equivalent, and particularly preferably 0.0001 to 0.1 equivalent.

The method which leads compound (IIa) to a sulfonamide represented by the formula (III) by sulfonating compound (IIa) with chlorosulfonic acid, followed by converting to sulfonyl chloride with phosphoryl chloride, and then reacting with ammonia, can be carried out according to a similar method to the known art (JP-B H05-36439).

The method which leads compound (IIb) to a sulfonamide represented by the formula (III) by hydrolyzing compound (IIb) can be carried out according to a similar method to the known art (Protective Groups in Organic Synthesis, page 275).

The reaction of the present invention has a feature that the substituent Z of 6-position is selectively substituted even when the substituent X of 2-position of imidazo[1,2-b] pyridazine ring is a halogen atom such as chlorine atom etc. Furthermore, the reaction of the present invention has a feature that the reaction proceeds without amide polar solvents such as HMPT (hexamethylphosphoric triamide) and DMA (dimethylacetamide) used in the prior art, which is suspected of toxicity. In addition, the reaction of the present invention proceeds at ice-cooling to room temperature in most cases with the exception of using palladium catalyst in toluene solvent, and heating such as disclosed in prior arts is not required.

EXAMPLES

Hereinafter, this invention will be further illustrated by Examples and Reference Examples, but this invention is not limited thereto. The elution in silica gel column chromatography was carried out under the observation by TLC (Thin Layer Chromatograph). In the observation by TLC, kieselgel 60F254 (70 to 230 mesh) manufactured by Merck was used as TLC plate, the solvent used as an eluting solvent in column chromatography was used as developing solvent, and a UV detector or iodine color-developing method was used for detection. As silica gel for column, kieselgel 60 (70 to 230 mesh) manufactured by Merck was used. In case that a mixed solvent was used as developing solvent, the numeric value shown in parentheses indicates volumetric mixing ratio of each solvents. NMR (nuclear magnetic resonance) spectra show proton NMR, and were determined with Bruker AV-400 (400 MHz) spectrometer with tetramethylsilane as internal standard, and all delta values are shown in ppm. The abbreviations used in the following Reference Examples and Examples have the following meanings.

s: singlet, d: doublet, t: triplet, q: quartet, m: multiplet, dd: double doublet, dt: double triplet, dq: double quartet, sept: septet, br: broad, brs: broad singlet, ddd: double double doublet, ddt: double double triplet, brd: broad doublet, brq: broad quartet, J: coupling constant, Hz: Hertz, Me: methyl group, Et: ethyl group, Pr: propyl group, i-Pr: isopropyl group, c-Pr: cyclopropyl group, Bu: butyl group, i-Bu: isobutyl group, dppp: 1,3-bis(diphenylphosphino)propane, PPh$_3$: triphenylphosphine, CDCl$_3$: heavy chloroform, DMSO-d$_6$: heavy dimethyl sulfoxide, DMF: N,N-dimethylformamide, HPLC: high performance liquid chromatography, %: weight %, mp: melting point, and room temperature means a temperature of 15 to 25° C.

Example 1

Synthesis of 6-ethyl-2-methylimidazo[1,2-b]pyridazine

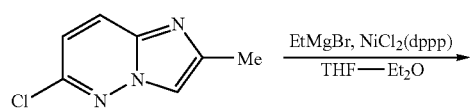

-continued

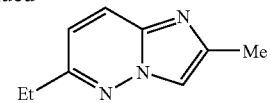

6-Chloro-2-methylimidazo[1,2-b]pyridazine (5.00 g, 29.8 mmol) and [1,3-bis(diphenylphosphino)propane]nickel(II) dichloride (0.08 g, 0.15 mmol) were suspended in dry ether (40 ml)-dry THF (20 ml), and a solution of ethylmagnesium bromide in ether (3 M, 15 ml, 45 mmol) was added dropwise thereto with stirring under ice-cooling over 5 minutes (internal temperature 10° C. or less). The temperature of the reaction solution was increased to room temperature, and the mixture was stirred at the same temperature for 2 hours and under reflux with heating for 3 hours. The reaction solution was left to cool to room temperature under stirring, and water (30 ml) was added little by little. Further, the pH of reaction mixture was adjusted to about 5 to 6 with concentrated hydrochloric acid under stirring at room temperature. The organic layer and the aqueous layer were separated from each other, and the aqueous layer was extracted with ethyl acetate (70 ml×2). The organic layers were combined and washed with water (250 ml×3). The organic layer was dried over magnesium sulfate and concentrated, and the residues were purified by silica gel column chromatography (chloroform:ethyl acetate=2:1→1:1), and the resulting crude oil was further purified by silica gel column chromatography (ethyl acetate), and the title compound was obtained as pale red oil. The yield was 1.32 g (27.4%).

$^1$H NMR (CDCl$_3$, δ): 1.33 (3H, t, J=7.5 Hz), 2.48 (3H, s), 2.82 (2H, q, J=7.5 Hz), 6.87 (1H, d, J=9.2 Hz), 7.65 (1H, s), 7.72 (1H, d, J=9.2 Hz)

IR (Neat, cm$^{-1}$): 2973, 2934, 2876, 1543, 1460, 1382, 1333, 1300, 1263, 1155, 1125, 1057, 1000, 820, 726, 699

Example 2

Synthesis of 6-ethyl-2-methylimidazo[1,2-b]pyridazin-3-sulfonamide

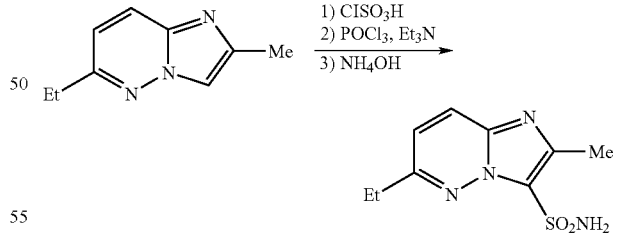

6-Ethyl-2-methylimidazo[1,2-b]pyridazine (2.70 g, 16.7 mmol) was dissolved in 1,2-dichloroethane (30 ml), and chlorosulfonic acid (1.27 g, 18.5 mmol) was added thereto under stirring at room temperature, and the mixture was stirred for 5 hours under reflux with heating. Then, the reaction solution was cooled to about 70° C., and triethylamine (2.38 g, 23.5 mmol) was added dropwise thereto over 1 minute. After dropping, the reaction solution was stirred for 20 minutes under reflux with heating. Thereafter, the reaction solution was cooled to about 70° C., and phosphorus oxychloride (3.86 g, 25.2 mmol) was added dropwise thereto over 1 minute. After dropping, the mixture was stirred for 2 hours under reflux with heating. The reaction solution was left to cool to about 50° C., and poured into 50 ml warm water (about 50° C.). The reaction mixture was stirred for 5 minutes, and the organic layer was separated. The aqueous layer was extracted with chloroform (50 ml×2). The organic layers were combined, washed with water, dried over magnesium sulfate, and concentrated. The residues were dissolved in acetonitrile (40 ml), and 14 N ammonia water (7 ml) was added thereto under stirring at room temperature, and the mixture was stirred at room temperature for 2 hours. After the reaction was completed, the reaction solution was poured onto ice-cold water (150 ml) and adjusted to about pH 4 with concentrated hydrochloric acid, to form crystals which were then collected by filtration, washed with water and dried under reduced pressure. Thereafter, the crystals were purified by silica gel column chromatography (chloroform:acetone=9:1→4:1). The title compound was obtained as white crystals. The yield was 1.8 g (44.7%).

mp 215.0-215.5° C.

$^1$H NMR (DMSO-$d_6$, δ): 1.30 (3H, t, J=7.5 Hz), 2.57 (3H, s), 2.93 (2H, q, J=7.5 Hz), 7.39 (1H, d, J=9.3 Hz), 7.47 (2H, brs), 8.08 (1H, d, J=9.3 Hz)

IR (Nujol, cm$^{-1}$): 3304, 3177, 3090, 1546, 1540, 1507, 1463, 1389, 1362, 1341, 1309, 1201, 1166, 1127, 1086, 1057, 959, 900, 9864, 824, 772, 686, 670, 652, 591, 525

Example 3

Synthesis of 2-chloro-6-n-propylimidazo[1,2-b]pyridazine

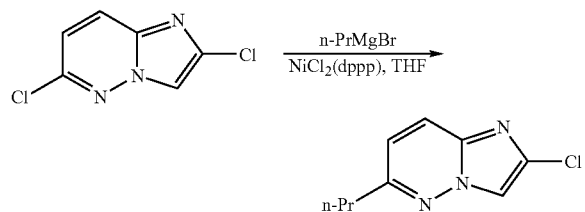

2,6-Dichloroimidazo[1,2-b]pyridazine (10.0 g, 53.2 mmol) and [1,3-bis(diphenylphosphino)propane]nickel(II) dichloride (0.43 g, 0.80 mmol) were added to tetrahydrofuran (80.0 ml) under a nitrogen stream, and a solution of n-propylmagnesium bromide in tetrahydrofuran (2 M, 31.9 ml, 63.8 mmol) was added dropwise thereto under ice-cooling over 60 minutes. The reaction mixture was stirred for 10 minutes under ice-cooling, warmed to room temperature, and stirred for 2 hours at room temperature. To the reaction mixture was added cold water (700 ml), and acidified with concentrated hydrochloric acid. Then the deposited solid was collected by filtration, and insoluble solid was washed with dilute hydrochloric acid, then with water. At the same time, the filtrate was extracted with ethyl acetate, the extracts were combined, and washed with dilute hydrochloric acid, saturated brine, saturated sodium hydrogen carbonate solution, and saturated brine, in that order. The resulting organic layer was dried over anhydrous magnesium sulfate, filtered, and concentrated. The concentrated residue and the solid collected by filtration were purified by silica gel column chromatography (ethyl acetate:hexane=3:7) to give the title compound as white crystals. The yield was 9.21 g (88.5%).

mp: 73.9-80.0° C.

$^1$H NMR (CDCl$_3$, δ): 1.01 (3H, t, J=7.4 Hz), 1.78 (2H, m), 2.79 (2H, t, J=7.6 Hz), 6.96 (1H, d, J=9.3 Hz), 7.75 (1H, d, J=9.3 Hz), 7.80 (1H, s).

IR (Nujol, cm$^{-1}$): 3122, 1466, 1377, 1314, 1302.

Example 4

Synthesis of 2-chloro-6-n-propylimidazo[1,2-b]pyridazin-3-sulfonamide

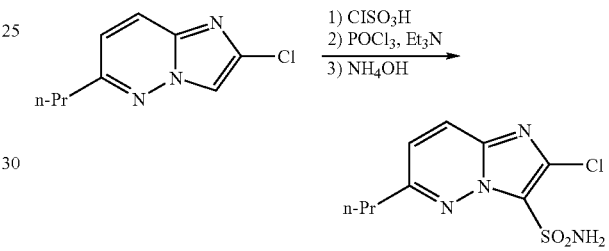

2-Chloro-6-n-propylimidazo[1,2-b]pyridazine (0.8 g, 4.1 mmol) and dichloroethane (10 ml) were introduced into a 200-ml eggplant type flask and stirred at room temperature, and chlorosulfonic acid (0.54 g, 4.5 mmol) was added thereto all at once, and the mixture was stirred for 4 hours under reflux with heating. The reaction solution was cooled to about 70° C., and triethylamine (0.5 g, 5 mmol) was added thereto all at once and stirred until the solid was dissolved, and phosphorus oxychloride (0.79 g, 5 mmol) was added thereto all at once, and the mixture was stirred for 2 hours under reflux with heating. After the reaction was completed, the reaction solution was left to cool, and water (50 ml) was added thereto and the organic phase was separated. The organic phase was washed with a saturated saline, dried over magnesium sulfate and concentrated. Acetonitrile (10 ml) and 28% ammonia water (4 ml) were added to the residue and stirred at room temperature for 2 hours. After the reaction was completed, water (100 ml) was added to the reaction solution, which was then adjusted to about pH 2 with dilute hydrochloric acid, and the formed crystals were collected by filtration, washed with water and chloroform, and dried under reduced pressure to give the title compound as pale brown crystals. The yield was 0.49 g (43.5%).

mp 174-5° C.

$^1$H NMR (DMSO-$d_6$, δ): 0.96 (3H, t, J=7.4 Hz), 1.7-1.9 (2H, m), 2.8-3.0 (2H, m), 7.53 (1H, d, J=9.5 Hz), 7.82 (2H, brs), 8.19 (1H, d, J=9.4 Hz)

IR (Nujol, cm$^{-1}$): 3377, 3324, 3189, 1545, 1364, 1322, 1187, 1166, 821, 680, 597

Example 5

Synthesis of 6-n-butyl-2-chloroimidazo[1,2-b]pyridazine

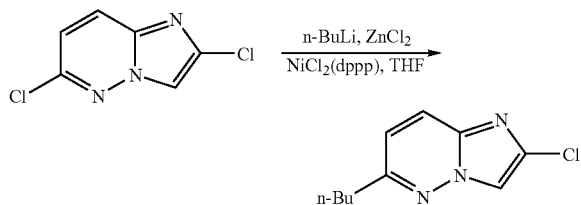

Zinc chloride (2.04 g, 15.0 mmol) was dried at 180° C. for 2 hours under vacuum and then cooled to room temperature, and anhydrous tetrahydrofuran (20.0 mL) was added thereto. n-Butyl lithium (1.6 M, 9.0 mL, 14.4 mmol) was added dropwise thereto over about 30 minutes under ice-cooling and stirred for 30 minutes under ice-cooling, to prepare a solution of n-butylzinc chloride in tetrahydrofuran. Separately, a suspension of 2,6-dichloroimidazo[1,2-b]pyridazine (1.88 g, 10.0 mmol) and [1,3-bis(diphenylphosphino)propane]nickel(II) dichloride (0.16 g, 0.30 mmol) in anhydrous tetrahydrofuran (20.0 mL) was prepared under a nitrogen atmosphere, and the previously prepared solution of n-butylzinc chloride in tetrahydrofuran was added dropwise thereto over 30 minutes with maintaining at 3 to 6° C. The mixture was stirred for 15 minutes under ice-cooling and for 3 hours at room temperature, poured into a saturated saline and adjusted to pH 2 with dilute hydrochloric acid. The reaction solution was extracted twice with ethyl acetate, and the extracts were combined, dehydrated over anhydrous magnesium sulfate and concentrated under reduced pressure. The residues were purified by silica gel column chromatography (ethyl acetate:hexane=1:4) to give the title compound as pale yellow crystals. The yield was 2.03 g (96.8%).

mp 61.0-63.0° C.

$^1$H NMR (CDCl$_3$, δ): 0.96 (3H, t, J=7.3 Hz), 1.41 (2H, tq, J=7.5, 7.3 Hz), 1.73 (2H, tt, J=7.8, 7.5 Hz), 2.81 (2H, t, J=7.8 Hz), 6.96 (1H, d, J=9.4 Hz), 7.74 (1H, d, J=9.4 Hz), 7.79 (1H, s).

IR (Nujol, cm$^{-1}$): 3115, 3061, 1545, 1466, 1378, 1326, 1276, 817.

Example 6

Synthesis of 6-n-butyl-2-chloroimidazo[1,2-b]pyridazin-3-ylsulfonamide

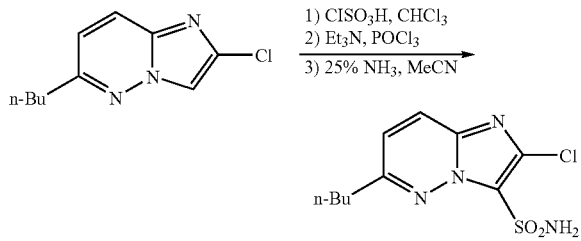

6-n-Butyl-2-chloroimidazo[1,2-b]pyridazine (1.00 g, 4.77 mmol) was dissolved in chloroform (10.0 mL), and chlorosulfonic acid (0.35 mL, 5.27 mmol) was added dropwise to the solution under stirring at room temperature. After the mixture was heated for 5 hours under reflux, it was confirmed by TLC that the starting material remained, so additional chlorosulfonic acid (0.35 mL, 5.27 mmol) was added thereto, and the mixture was heated for 4 hours under reflux. The resulting suspension was left to cool to room temperature, and triethylamine (2.50 mL, 17.9 mmol) and phosphorus oxychloride (2.00 mL, 21.5 mmol) were added thereto, and the mixture was heated again for 4 hours under reflux. The reaction solution was cooled to room temperature, poured into water and extracted 3 times with chloroform, and the extracts were combined, dehydrated over anhydrous magnesium sulfate and concentrated under reduced pressure to give 3.24 g dark red liquid. This liquid was dissolved in acetonitrile (10.0 mL) and added dropwise to a solution of 25% ammonia water (5.00 g, 73.5 mmol) in acetonitrile (15.0 mL) under ice-cooling. The mixture was stirred for 30 minutes under ice-cooling and for 1 hour at room temperature, and then the acetonitrile was distilled away under reduced pressure. The residues were adjusted to pH 2 with dilute hydrochloric acid and extracted twice with chloroform, and the chloroform layers were combined, dehydrated over anhydrous magnesium sulfate and concentrated under reduced pressure. The residues were purified by silica gel column chromatography (ethyl acetate:hexane=1:1→chloroform:ethanol=20:1) to give the title compound as white crystals. The yield was 0.92 g (66.8%).

mp 165.5-166.5° C.

$^1$H NMR (DMSO-d$_6$, δ): 0.93 (3H, t, J=7.3 Hz), 1.37 (2H, tq, J=7.5, 7.3 Hz), 1.72 (2H, tt, J=7.9, 7.5 Hz), 2.93 (2H, t, J=7.9 Hz), 7.53 (1H, d, J=9.4 Hz), 7.80 (2H, s), 8.18 (1H, d, J=9.4 Hz).

IR (Nujol, cm$^{-1}$): 3412, 3360, 3287, 3197, 1546, 1464, 1376, 1321, 1172.

Example 7

Synthesis of N'-(2-chloro-6-cyclopropylimidazo[1,2-b]pyridazin-3-ylsulfonyl)-N,N-diisobutylformamidine

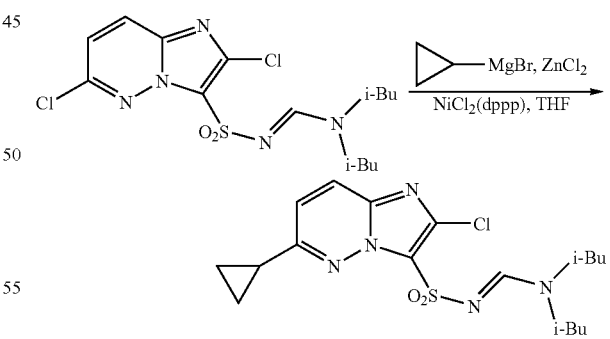

Magnesium metal powder (0.27 g, 11.1 mmol) was mixed with iodine (5 mg), heated with a dryer under a nitrogen atmosphere and cooled to room temperature, and anhydrous tetrahydrofuran (15.0 mL) was added thereto. Cyclopropyl bromide (1.33 g, 1.10 mmol), while keeping at 28 to 33° C., was added dropwise to the mixture under stirring at room temperature, and then the mixture was stirred at room temperature for 30 minutes to prepare a pale yellowish gray solution of cyclopropylmagnesium bromide in tetrahydrofuran. Separately, zinc chloride (1.50 g, 11.0 mmol) dried at 180° C. for 4 hours under vacuum was dissolved in anhydrous tetrahydrofuran (10.0 mL) under a nitrogen atmosphere and then the previously prepared solution of cyclopropylmagnesium bromide in tetrahydrofuran was added dropwise thereto with keeping at 0° C. or less with an ice-sodium chloride bath. The mixture was stirred at about −10° C. for 15 minutes, and [1,3-bis(diphenylphosphino)propane]nickel(II) dichloride (0.27 g, 0.50 mmol) was added as powder to the resulting suspension, and then a solution of N'-(2,6-dichloroimidazo[1,2-b]pyridazin-3-ylsulfonyl)-N,N-diisobutylformamidine (2.03 g, 5.00 mmol) dissolved in anhydrous tetrahydrofuran (10.0 mL) was added dropwise thereto. The mixture was stirred at −10° C. for 2 hours, then at room temperature for 16 hours, poured into a saturated saline, adjusted to pH 2 with dilute hydrochloric acid, and extracted 4 times with chloroform. The extracts were combined, dehydrated over anhydrous magnesium sulfate, concentrated under reduced pressure, and the residues were purified by silica gel column chromatography (ethyl acetate: hexane=1:1), whereby 0.64 g (31.5%) of the starting material N'-(2,6-dichloroimidazo[1,2-b]pyridazin-3-ylsulfonyl)-N,N-diisobutylformamidine was recovered and simultaneously the title compound was obtained as pale yellow crystals. The yield was 0.94 g (45.7%).

mp 154.0-160.0° C.

$^1$H NMR (CDCl$_3$, δ): 0.74 (6H, d, J=6.7 Hz), 0.95 (6H, d, J=6.7 Hz), 1.00-1.10 (2H, m), 1.10-1.25 (2H, m), 1.85-2.10 (2H, m), 2.10-2.20 (1H, m), 3.19 (2H, d, J=7.5 Hz), 3.28 (2H, d, J=7.5 Hz), 6.98 (1H, d, J=9.4 Hz), 7.78 (1H, d, J=9.4 Hz), 8.45 (1H, s).

IR (Nujol) ν (cm$^{-1}$): 1613, 1464, 1334, 1318, 1143, 909, 859, 661.

Example 8

Synthesis of 2-chloro-6-cyclopropylimidazo[1,2-b]pyridazin-3-ylsulfonamide

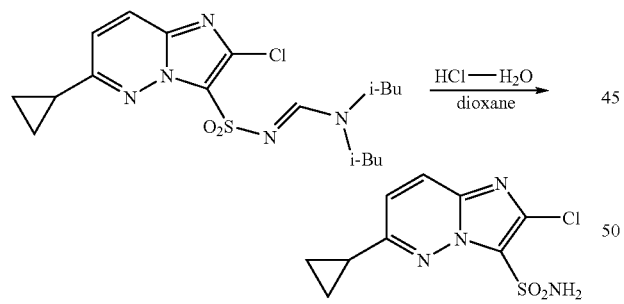

N'-(2-Chloro-6-cyclopropylimidazo[1,2-b]pyridazin-3-ylsulfonyl)-N,N-diisobutylformamidine (0.93 g, 2.26 mmol) was dissolved in dioxane (9.00 mL), and 36% concentrated hydrochloric acid (9.0 mL, 107 mmol) was added dropwise to the solution under stirring at 100° C. The mixture was stirred for 15 hours at 100 to 105° C., then left to cool to room temperature and concentrated under reduced pressure until crystals occurred. Water (30.0 mL) was poured into the residues, and the crystals were completely precipitated, then filtered, washed with water and washed with methanol, to give the title compound as white crystals. The yield was 0.31 g (50.4%).

mp 194.0-196.0° C.

NMR (DMSO-d$_6$, δ): 1.10-1.25 (4H, m), 2.30-2.45 (1H, m), 7.36 (1H, d, J=9.4 Hz), 7.78 (2H, brs), 8.12 (1H, d, J=9.4 Hz).

IR (Nujol, cm$^{-1}$): 3348, 3247, 1553, 1468, 1455, 1358, 1316, 1170, 908, 825, 662.

Example 9

Synthesis of N'-(2-chloro-6-ethenylimidazo[1,2-b]pyridazin-3-ylsulfonyl)-N,N-diisobutylformamidine

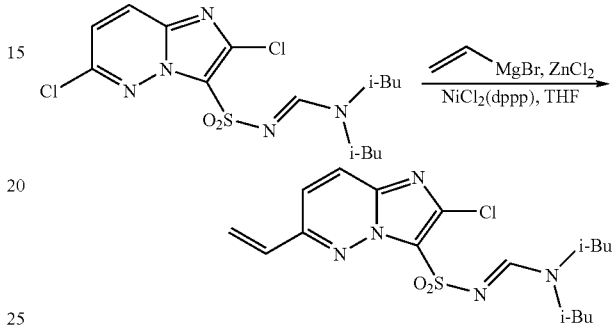

The title compound was obtained as pale yellow crystals by the same reaction as in Example 7 except that a solution of commercially available vinyl magnesium bromide in tetrahydrofuran was used in place of the solution of cyclopropylmagnesium bromide in tetrahydrofuran, and [1,3-bis(diphenylphosphino)propane]nickel(II) dichloride was used in an amount of 3 mol-% relative to the starting material N'-(2,6-dichloroimidazo[1,2-b]pyridazin-3-ylsulfonyl)-N,N-diisobutylformamidine. The yield was 80.4%.

mp 194.0-198.0° C.

$^1$H NMR (CDCl$_3$, δ): 0.71 (6H, d, J=6.7 Hz), 0.94 (6H, d, J=6.6 Hz), 1.85-2.10 (2H, m), 3.17 (2H, d, J=7.5 Hz), 3.26 (2H, d, J=7.7 Hz), 5.77 (1H, d, J=11.1 Hz), 6.16 (1H, d, J=17.8 Hz), 6.82 (1H, dd, J=17.8, 11.1 Hz), 7.46 (1H, d, J=9.5 Hz), 7.89 (1H, d, J=9.5 Hz), 8.50 (1H, s).

IR (Nujol, cm$^{-1}$): 1614, 1456, 1350, 1319, 1145, 913, 859, 664, 612.

Example 10

Synthesis of 2-chloro-6-ethenylimidazo[1,2-b]pyridazin-3-ylsulfonamide

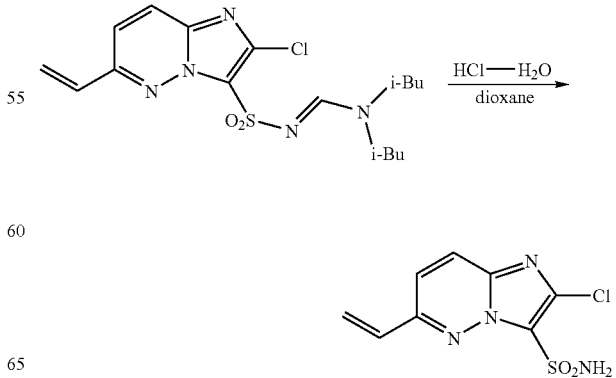

The reaction was carried out in the same manner as in Example 8 except that N'-(2-chloro-6-ethenylimidazo[1,2-b]pyridazin-3-ylsulfonyl)-N,N-diisobutylformamidine was used in place of N'-(2-chloro-6-cyclopropylimidazo[1,2-b]pyridazin-3-ylsulfonyl)-N,N-diisobutylformamidine. The resulting crystals were purified by silica gel column chromatography (chloroform:methanol=10:1) to give the title compound as white crystals. The yield was 42.1%.

mp 229.0-233.0° C.

$^1$H NMR (DMSO-d$_6$, δ): 5.87 (1H, d, J=11.2 Hz), 6.50 (1H, d, J=17.9 Hz), 6.86 (1H, dd, J=17.9, 11.2 Hz), 7.89 (2H, s), 7.96 (1H, d, J=9.6 Hz), 8.26 (1H, d, J=9.6 Hz).

IR (Nujol, cm$^{-1}$): 3316, 3183, 1466, 1368, 1321, 1167.

Example 11

Synthesis of N'-(2-chloro-6-(1-propenyl)imidazo[1,2-b]pyridazin-3-ylsulfonyl)-N,N-diisobutylformamidine

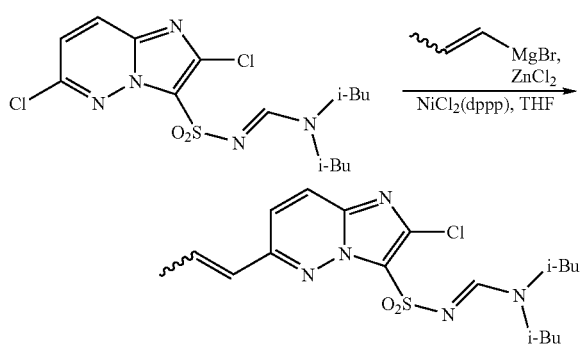

The title compound was obtained as a mixture of E and Z (E:Z=5:3) in the form of pale yellow crystals by the same reaction as in Example 7 except that a solution of commercially available 1-propenylmagnesium bromide in tetrahydrofuran was used in place of the solution of cyclopropylmagnesium bromide in tetrahydrofuran, and [1,3-bis(diphenylphosphino)propane]nickel(II) dichloride was used in an amount of 3 mol-% relative to the starting material N'-(2,6-dichloroimidazo[1,2-b]pyridazin-3-ylsulfonyl)-N,N-diisobutylformamidine. The yield was 100%. mp: not be measured because of a mixture of E and Z.

$^1$H NMR (CDCl$_3$, δ): [E isomer] 0.72 (6H, d, J=6.6 Hz), 0.94 (6H, d, J=6.6 Hz), 1.85-2.10 (2H, m), 2.00 (3H, dd, J=6.9, 1.5 Hz), 3.17 (2H, d, J=7.6 Hz), 3.26 (2H, d, J=7.7 Hz), 6.51 (1H, dq, J=16.0, 1.5 Hz), 6.71 (1H, dq, J=16.0, 6.9 Hz), 7.35 (1H, d, J=9.5 Hz), 7.82 (1H, d, J=9.5 Hz), 8.50 (1H, s).

$^1$H NMR (CDCl$_3$, δ): [Z isomer] 0.72 (6H, d, J=6.6 Hz), 0.92 (6H, d, J=6.6 Hz), 1.85-2.10 (2H, m), 2.21 (3H, dd, J=7.3, 1.8 Hz), 3.12 (2H, d, J=7.5 Hz), 3.25 (2H, d, J=7.7 Hz), 6.23 (1H, dq, J=11.9, 7.3 Hz), 6.40 (1H, dq, J=11.9, 1.8 Hz), 7.19 (1H, d, J=9.5 Hz), 7.85 (1H, d, J=9.5 Hz), 8.43 (1H, s).

IR (Nujol, cm$^{-1}$): 1609, 1456, 1351, 1319, 1144, 911.

Example 12

Synthesis of (E)-2-chloro-6-(1-propenyl)imidazo[1,2-b]pyridazin-3-ylsulfonamide

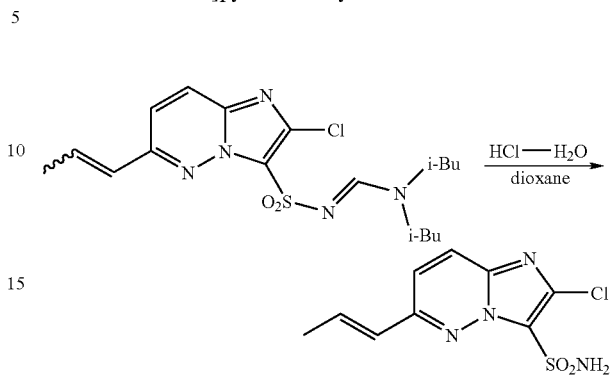

The reaction was carried out in the same manner as in Example 8 except that N'-(2-chloro-6-(1-propenyl)imidazo[1,2-b]pyridazin-3-ylsulfonyl)-N,N-diisobutylformamidine as a mixture of E and Z was used in place of N'-(2-chloro-6-cyclopropylimidazo[1,2-b]pyridazin-3-ylsulfonyl)-N,N-diisobutylformamidine. The resulting crystals were purified by silica gel column chromatography (chloroform:methanol=20:1) to give the title compound as white crystals. The yield was 70.1%.

mp 225.0-229.0° C.

$^1$H NMR (DMSO-d$_6$, δ): 1.98 (3H, dd, J=6.8, 1.7 Hz), 6.71 (1H, dq, J=16.0, 1.7 Hz), 7.01 (1H, dq, J=16.0, 6.8 Hz), 7.83 (2H, s), 7.84 (1H, d, J=9.5 Hz), 8.19 (1H, d, J=9.6 Hz).

IR (Nujol, cm$^{-1}$): 3323, 3179, 1662, 1550, 1466, 1360, 1325, 1173.

Example 13

Synthesis of 2-chloro-6-isobutylimidazo[1,2-b]pyridazine

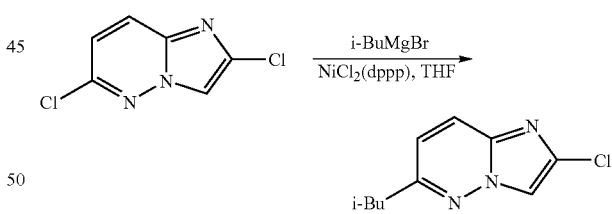

The reaction was carried out in the same manner as in Example 3 except that a solution of isobutylmagnesium bromide in tetrahydrofuran was used in place of the solution of n-propylmagnesium bromide in tetrahydrofuran. The resulting crude product was purified by silica gel column chromatography (ethyl acetate:hexane=1:4) to give the title compound as pale yellow crystals. The yield was 1.27 g (60.6%).

mp 71.0-72.5° C.

$^1$H NMR (CDCl$_3$, δ): 0.98 (6H, d, J=6.6 Hz), 2.09 (1H, m), 2.68 (2H, d, J=7.3 Hz), 6.94 (1H, d, J=9.3 Hz), 7.75 (1H, d, J=9.3 Hz), 7.81 (1H, s).

IR (Nujol, cm$^{-1}$): 3126, 3059, 1545, 1466, 1369, 1331, 1320, 1279, 803.

Example 14

Synthesis of 2-chloro-6-isobutylimidazo[1,2-b]pyridazin-3-ylsulfonamide

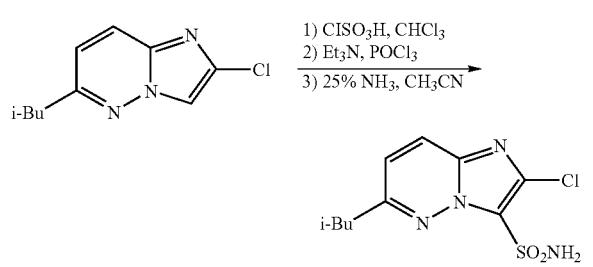

The reaction was carried out in the same manner as in Example 6 except that 2-chloro-6-isobutylimidazo[1,2-b]pyridazine was used in place of 2-chloro-6-n-butylimidazo[1,2-b]pyridazine. The resulting reaction mixture was purified by silica gel column chromatography (ethyl acetate: hexane=1:1) to give the title compound as white crystals. The yield was 1.12 g (64.0%).

mp 168.0-169.5° C.

$^1$H NMR (DMSO-d$_6$, δ): 0.93 (6H, d, J=6.6 Hz), 2.14 (1H, m), 2.82 (2H, d, J=7.4 Hz), 7.51 (1H, d, J=9.4 Hz), 7.80 (2H, s), 8.19 (1H, d, J=9.4 Hz).

IR (Nujol, cm$^{-1}$): 3316, 3180, 3117, 1548, 1469, 1362, 1336, 1321, 1200, 1173, 849, 678.

Example 15

Synthesis of 2-chloro-6-ethylimidazo[1,2-b]pyridazine

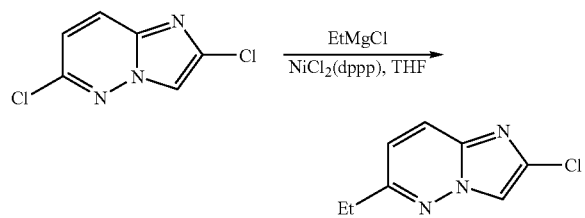

The title compound was obtained as pale yellow crystals by the same reaction as in Example 3 except that a solution of ethylmagnesium chloride in tetrahydrofuran was used in place of the solution of n-propylmagnesium bromide in tetrahydrofuran. The yield was 66.2%.

$^1$H NMR (CDCl$_3$, δ): 1.35 (3H, t, J=7.6 Hz), 2.85 (2H, q, J=7.6 Hz), 6.97 (1H, d, J=9.3 Hz), 7.75 (1H, d, J=9.3 Hz), 7.80 (1H, s).

IR (Nujol, cm$^1$): 3121, 3058, 1544, 1471, 1318, 1280, 1262, 1189, 1142, 1121, 1059, 983, 953, 822.

Example 16

Synthesis of 2-chloro-6-ethylimidazo[1,2-b]pyridazin-3-ylsulfonamide

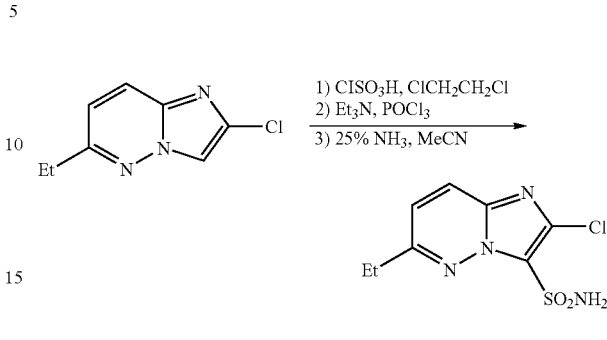

The title compound was obtained as pale brown crystals by the same reaction as in Example 4 except that 2-chloro-6-ethylimidazo[1,2-b]pyridazine was used in place of 2-chloro-6-n-propylimidazo[1,2-b]pyridazine. The yield was 74.1%.

mp 204-205° C.

$^1$H NMR (DMSO-d$_6$, δ): 1.31 (3H, t, J=7.6 Hz), 2.95 (2H, q, J=7.6 Hz), 7.54 (1H, d, J=9.4 Hz), 7.82 (2H, brs), 8.19 (1H, d, J=9.4 Hz).

IR (Nujol, cm$^{-1}$): 3317, 3211, 1365, 1356, 1325, 1172, 829, 668.

Example 17

Synthesis of 2-methyl-6-n-propylimidazo[1,2-b]pyridazine

The title compound was obtained as pale reddish oil by the same reaction as in Example 1 except that a solution of n-propylmagnesium chloride in ether was used in place of the solution of ethylmagnesium bromide in ether, and as the solvent, a tetrahydrofuran solvent was used in place of the mixed solvent of ether and tetrahydrofuran. The yield was 19.1%.

$^1$H NMR (CDCl$_3$, δ): 1.00 (3H, t, J=7.4 Hz), 1.7-1.9 (2H, m), 2.48 (3H, d, J=0.7 Hz), 2.77 (2H, t, J=7.5 Hz), 6.85 (1H, d, J=9.2 Hz), 7.66 (1H, d, J=0.7 Hz), 7.72 (1H, d, J=9.2 Hz).

IR (Nujol, cm$^{-1}$): 2961, 1541, 1464, 1326, 1296, 1153, 1124, 989, 816, 726.

Example 18

Synthesis of 2-methyl-6-n-propylimidazo[1,2-b]pyridazin-3-ylsulfonamide

-continued

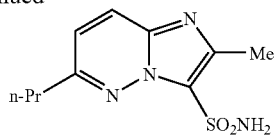

The title compound was obtained as pale brown crystals by the same reaction as in Example 4 except that 2-methyl-6-n-propylimidazo[1,2-b]pyridazine was used in place of 2-chloro-6-n-propylimidazo[1,2-b]pyridazine. The yield was 14.6%.

mp 178-179° C. (dec.)

$^1$H NMR (DMSO-$d_6$, δ): 0.96 (3H, t, J=7.3 Hz), 1.7-1.9 (2H, m), 2.56 (3H, s), 2.8-2.9 (2H, m), 7.39 (1H, d, J=9.3 Hz), 7.46 (2H, brs), 8.08 (1H, d, J=9.3 Hz).

IR (Nujol, cm$^1$): 3384, 3327, 1543, 1508, 1420, 1348, 1327, 1309, 1162, 827.

Example 19

Synthesis of N,N-dimethyl-N'-(6-n-propyl-2-trifluoromethylimidazo[1,2-b]pyridazin-3-ylsulfonyl)formamidine

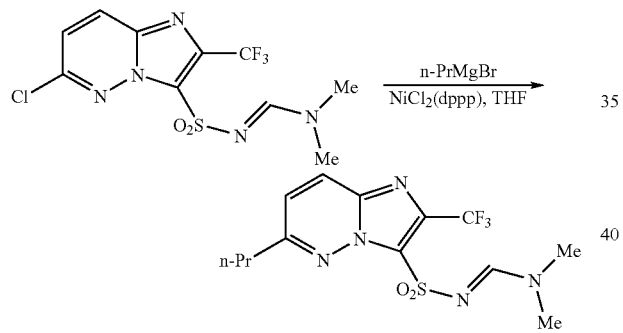

To a suspension of N'-(6-chloro-2-trifluoromethylimidazo[1,2-b]pyridazin-3-ylsulfonyl)-N,N-dimethylformamidine (1.00 g, 2.81 mmol) and [1,3-bis(diphenylphosphino)propane]nickel(II) dichloride (0.076 g, 0.14 mmol) in tetrahydrofuran (8.0 ml) was added dropwise a solution of n-propylzinc bromide in tetrahydrofuran (0.5 M, 8.43 ml, 4.22 mmol) with stirring under ice-cooling and nitrogen stream. The reaction mixture was stirred for 30 minutes under ice-cooling and 4.5 hours at room temperature, then poured into cold water and made acid with dilute hydrochloric acid. The precipitated solid was collected by filtration, washed with dilute hydrochloric acid, then water, and purified by silica gel column chromatography (ethyl acetate:chloroform=2:5) to give the title compound as white crystals. The yield was 0.62 g (60.7%).

mp 219.3-220.4° C.

$^1$H NMR (DMSO-$d_6$, δ): 0.95 (3H, t, J=7.3 Hz), 1.71 (2H, m), 2.88 (2H, t, J=7.7 Hz), 2.92 (3H, s), 3.28 (3H, s), 7.59 (1H, d, J=9.5 Hz), 8.33 (1H, d, J=9.5 Hz), 8.54 (1H, s).

IR (Nujol, cm$^{-1}$): 1635, 1334, 1318, 1169, 1153, 920, 619.

Example 20

Synthesis of 6-n-propyl-2-trifluoromethylimidazo[1,2-b]pyridazin-3-ylsulfonamide

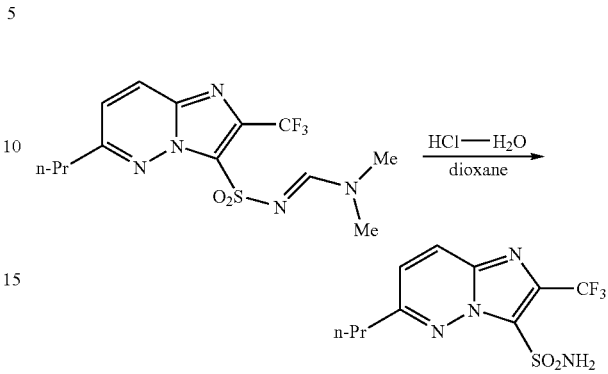

N,N-dimethyl-N'-(6-n-propyl-2-trifluoromethylimidazo[1,2-b]pyridazin-3-ylsulfonyl)formamidine (0.30 g, 0.83 mmol) was dissolved in dioxane (10.0 ml), and to the solution was added concentrated hydrochloric acid (5.0 ml) and stirred at 60° C. for 2 hours, 80° C. for 2 hours and 90° C. for 2 hours. The reaction mixture was concentrated under reduced pressure. To the residues was added water, and adjusted pH to 3 with aqueous 1N sodium hydroxide solution. The precipitated solid was collected by filtration, and washed with water to give the title compound as white crystals. The yield was 0.24 g (94.3%).

mp 151.0-151.7° C.

$^1$H NMR (DMSO-$d_6$, δ): 0.97 (3H, t, J=7.3 Hz), 1.78 (2H, m), 2.96 (2H, t, J=7.7 Hz), 7.62 (1H, d, J=9.5 Hz), 7.97 (2H, brs), 8.36 (1H, d, J=9.5 Hz).

IR (Nujol, cm$^{-1}$): 3356, 1550, 1465, 1373, 1362, 1322, 1199, 1179, 1151, 608.

Example 21

Synthesis of 2-chloro-6-n-propylimidazo[1,2-b]pyridazine

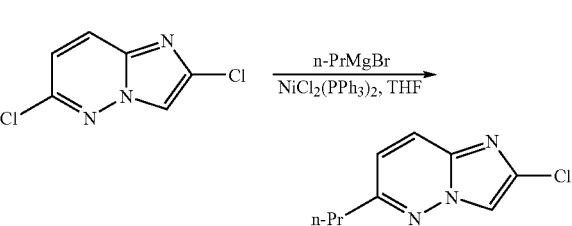

2,6-Dichloroimidazo[1,2-b]pyridazine (0.50 g, 2.66 mmol) and bis(triphenylphosphine)nickel(II) dichloride (0.17 g, 0.27 mmol) were added to tetrahydrofuran (5.0 ml) under a nitrogen stream, and a solution of n-propylmagnesium bromide in tetrahydrofuran (2 M, 1.99 ml, 3.99 mmol) was added dropwise over 10 minutes to the mixture under ice-cooling. The mixture was stirred for 10 minutes under ice-cooling, and the reaction mixture was warmed to room temperature and stirred for 4 hours at room temperature. Cold water (50 ml) was added to the reaction mixture which was then acidified with dilute hydrochloric acid, and extracted with ethyl acetate. The extracts were washed with dilute hydrochloric acid, a saturated saline, an aqueous saturated sodium bicarbonate solution and a saturated saline in this order. The resulting organic layer was dried over anhydrous magnesium sulfate, filtrated and concentrated. The concentrated residue was purified by silica gel column chromatography (ethyl acetate:hexane=3:7) to give the title compound as white crystals. The yield was 0.21 g (40.4%).

Example 22

Synthesis of 2-chloro-6-n-propylimidazo[1,2-b]pyridazine

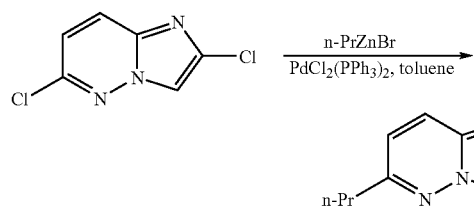

Under a nitrogen stream, a solution of n-propylzinc bromide in tetrahydrofuran (0.5 M, 7.98 ml, 3.99 mmol) was diluted with toluene (5.0 ml), and 2,6-dichloroimidazo[1,2-b]pyridazine (0.50 g, 2.66 mmol) and bis(triphenylphosphine)palladium(II) dichloride (0.19 g, 0.27 mmol) were added thereto, and the reaction mixture was stirred for 2 hours at 80° C. After cooling, to the reaction mixture was added cold water (50 ml), acidified with dilute hydrochloric acid, extracted with ethyl acetate, and the extracts were washed with dilute hydrochloric acid, a saturated saline, an aqueous saturated sodium bicarbonate solution and a saturated saline in this order. The resulting organic layer was dried over anhydrous magnesium sulfate, filtrated and concentrated. The concentrated residue was purified by silica gel column chromatography (ethyl acetate:hexane=3:7) to give the title compound as white crystals. The yield was 0.31 g (59.6%).

Example 23

Synthesis of 2-chloro-6-n-propylimidazo[1,2-b]pyridazine

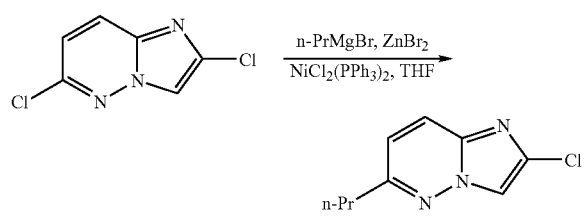

Under a nitrogen stream, 2,6-dichloroimidazo[1,2-b]pyridazine (1.00 g, 5.32 mmol), bis(triphenylphosphine)nickel (II) dichloride (0.10 g, 0.16 mmol) and zinc bromide (0.04 g, 0.16 mmol) were added to tetrahydrofuran (8.0 ml), and a solution of n-propylmagnesium bromide in tetrahydrofuran (2 M, 3.99 ml, 7.98 mmol) was added dropwise over 10 minutes to the mixture under ice-cooling. The reaction mixture was stirred for 10 minutes under ice-cooling, and warmed to room temperature and stirred for 4 hours at room temperature. Cold water (100 ml) was added to the reaction mixture which was then acidified with dilute hydrochloric acid, and extracted with ethyl acetate. The extracts were washed with dilute hydrochloric acid, a saturated saline, an aqueous saturated sodium bicarbonate solution and a saturated saline in this order. The resulting organic layer was dried over anhydrous magnesium sulfate, filtrated and concentrated. The concentrated residue was purified by silica gel column chromatography (ethyl acetate:hexane=3:7) to give the title compound as pale yellow crystals. The yield was 0.76 g (73.1%).

Example 24

Synthesis of 2-chloro-6-n-propylimidazo[1,2-b]pyridazine

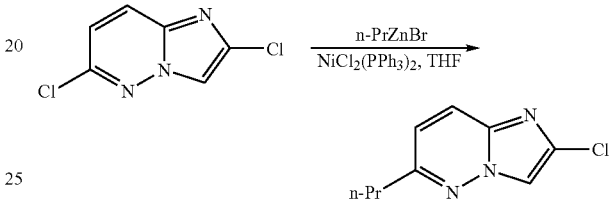

Under a nitrogen stream, 2,6-dichloroimidazo[1,2-b]pyridazine (0.50 g, 2.66 mmol) and bis(triphenylphosphine)nickel(II) dichloride (0.17 g, 0.27 mmol) were added to tetrahydrofuran (5.0 ml), and a solution of n-propylzinc bromide in tetrahydrofuran (0.5 M, 7.98 ml, 3.99 mmol) was added dropwise over 10 minutes to the mixture under ice-cooling. The reaction mixture was stirred for 10 minutes under ice-cooling, and warmed to room temperature and stirred for 2 hours at room temperature. Cold water (50 ml) was added to the reaction mixture which was then acidified with dilute hydrochloric acid, and extracted with ethyl acetate. The extracts were washed with dilute hydrochloric acid, a saturated saline, an aqueous saturated sodium bicarbonate solution and a saturated saline in this order. The resulting organic layer was dried over anhydrous magnesium sulfate, filtrated and concentrated. The concentrated residue was purified by silica gel column chromatography (ethyl acetate:hexane=3:7) to give the title compound as white crystals. The yield was 0.43 g (82.7%).

Example 25

Synthesis of 2-chloro-6-n-propylimidazo[1,2-b]pyridazine

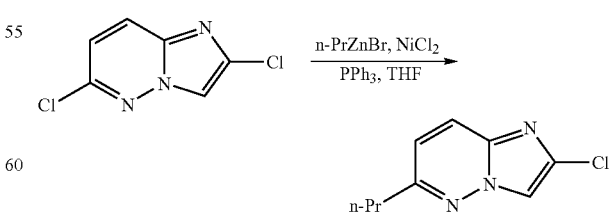

Under a nitrogen stream, anhydrous nickel(II) chloride (0.036 g, 0.27 mmol) and triphenylphosphine (0.15 g, 0.53 mmol) were added to tetrahydrofuran (5.0 ml), and stirred for 1 hour at room temperature. To this mixed solution was added 2,6-dichloroimidazo[1,2-b]pyridazine (0.50 g, 2.66 mmol), and a solution of n-propylzinc bromide in tetrahydrofuran (0.5 M, 7.98 ml, 3.99 mmol) was added dropwise thereto over 10 minutes under ice-cooling. The reaction mixture was stirred for 10 minutes under ice-cooling, and warmed to room temperature and stirred for 2 hours at room temperature. Cold water (50 ml) was added to the reaction mixture which was then acidified with dilute hydrochloric acid, and extracted with ethyl acetate. The extracts were washed with dilute hydrochloric acid, a saturated saline, an aqueous saturated sodium bicarbonate solution and a saturated saline in this order. The resulting organic layer was dried over anhydrous magnesium sulfate, filtrated and concentrated. The concentrated residue was purified by silica gel column chromatography (ethyl acetate:hexane=3:7) to give the title compound as white crystals. The yield was 0.46 g (88.5%).

Example 26

Synthesis of 2-chloro-6-n-propylimidazo[1,2-b]pyridazine

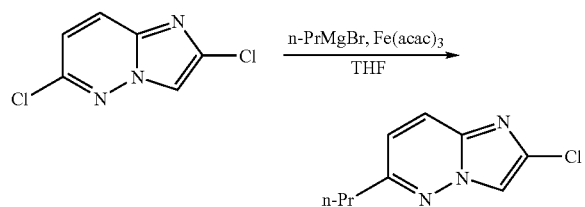

Under a nitrogen stream, 2,6-dichloroimidazo[1,2-b]pyridazine (0.50 g, 2.66 mmol) and iron(III) acetylacetonate (0.094 g, 0.27 mmol) were added to tetrahydrofuran (5.0 ml), and a solution of n-propylmagnesium bromide in tetrahydrofuran (2 M, 1.99 ml, 3.99 mmol) was added dropwise over 13 minutes to the mixture with stirring at 0 to 10° C. After stirring for 10 minutes under ice-cooling, the reaction mixture was warmed to room temperature and stirred for 6 hours at room temperature. The reaction mixture was poured onto ice-cold water, acidified with concentrated hydrochloric acid, and extracted with ethyl acetate. The extracts were washed with dilute hydrochloric acid, an aqueous saturated sodium bicarbonate solution and a saturated saline. The resulting organic layer was dried over anhydrous magnesium sulfate, filtrated and concentrated. The residue was purified by silica gel column chromatography (ethyl acetate:hexane=3:7) to give the title compound as pale yellow crystals. The yield was 0.28 g (53.8%).

Reference Example 1

Synthesis of N'-(2,6-dichloroimidazo[1,2-b]pyridazin-3-ylsulfonyl)-N,N-dimethylformamidine

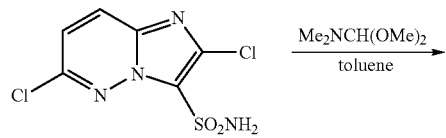

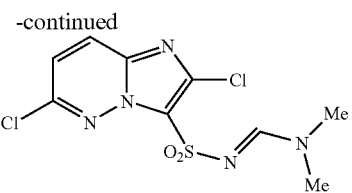

2,6-Dichloroimidazo[1,2-b]pyridazin-3-ylsulfonamide (2.00 g, 6.22 mmol) and N,N-Dimethylformamide dimethyl acetal (1.80 ml, 13.5 mmol) were heated under reflux for 4 hours in toluene (20.0 ml). The resulting reaction solution was left to cool to room temperature, and concentrated to dryness under reduced pressure to give the title compound as pale yellow crystals. The yield was 2.36 g (100%).

$^1$H NMR (DMSO-$d_6$, δ): 2.94 (3H, s), 3.26 (3H, s), 7.71 (1H, d, J=9.5 Hz), 8.34 (1H, d, J=9.5 Hz), 8.43 (1H, s).

Reference Example 2

Synthesis of N'-(2,6-dichloroimidazo[1,2-b]pyridazin-3-ylsulfonyl)-N,N-diisobutylformamidine

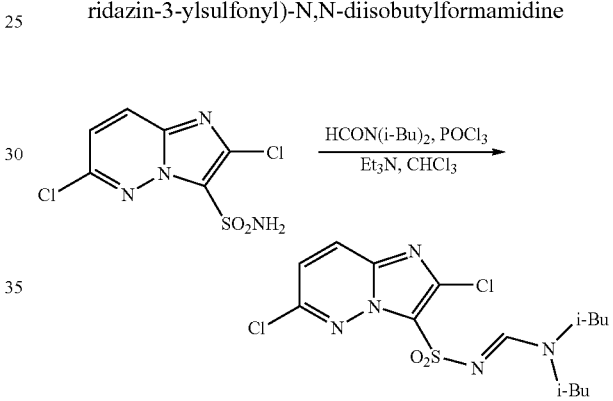

N,N-Diisobutylformamide (5.44 g, 34.5 mmol) was dissolved in chloroform (25.0 mL), and under cooling in an ice-sodium chloride bath, phosphorus oxychloride (3.22 mL, 34.5 mmol) was added dropwise thereto at −2° C. or less. After stirring at −2° C. or less for 30 minutes, to the mixture was added 2,6-dichloroimidazo[1,2-b]pyridazin-3-ylsulfonamide (6.15 g, 23.0 mmol). The mixture was stirred at −10° C. for 10 minutes, and triethylamine (19.3 mL, 138 mmol) was added dropwise over 20 minutes to the solution at 5° C. or less. The mixture was stirred for 1 hour at 0° C. or less and for 1 hour at room temperature, then poured into an aqueous saturated sodium bicarbonate and extracted 5 times with chloroform. The extracts were combined, dehydrated over anhydrous magnesium sulfate, and concentrated under reduced pressure. The residues were purified by silica gel column chromatography (ethyl acetate:hexane=1:1) to give the title compound as pale yellow crystals. The yield was 5.58 g (59.6%).

mp 151.0-154.0° C.

$^1$H NMR (CDCl$_3$, δ): 0.76 (6H, d, J=6.7 Hz), 0.97 (6H, d, J=6.7 Hz), 1.90-2.10 (2H, m), 3.23 (2H, d, J=7.6 Hz), 3.28 (2H, d, J=7.7 Hz), 7.26 (1H, d, J=9.5 Hz), 7.90 (1H, d, J=9.5 Hz), 8.51 (1H, s).

IR (Nujol, cm$^{-1}$): 1615, 1456, 1324, 1311, 1146, 910, 858, 654.

Reference Example 3

Synthesis of N'-(6-chloro-2-trifluoromethylimidazo [1,2-b]pyridazin-3-ylsulfonyl)-N,N-dimethylformamidine

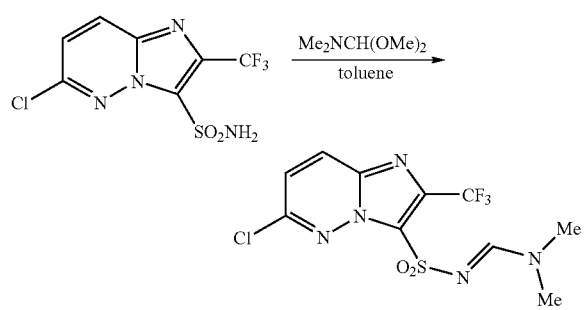

6-Chloro-2-trifluoromethylimidazo[1,2-b]pyridazin-3-ylsulfonamide (1.70 g, 5.65 mmol) was suspended in toluene (10.0 ml), and N,N-dimethylformamide dimethyl acetal (90%, 1.84 ml, 12.4 mmol) was added thereto and stirred for 3.5 hours under reflux. The reaction mixture was concentrated under reduced pressure. To the residue concentrated was added diisopropyl ether, and the crystals were collected by filtration to give the title compound as brown crystals. The yield was 1.96 g (97.4%).

mp 203.7-205.0° C.

$^1$H NMR (CDCl$_3$, δ): 2.95 (3H, s), 3.29 (3H, s), 7.79 (1H, d, J=9.6 Hz), 8.47 (1H, s), 8.52 (1H, d, J=9.6 Hz).

IR (Nujol, cm$^{-1}$): 1636, 1526, 1456, 1321, 1201, 1159, 1130, 1115, 922, 816, 628, 616.

INDUSTRIAL APPLICABILITY

According to the present invention, it becomes possible to produce easily and inexpensively an imidazo[1,2-b]pyridazin-3-ylsulfonamide derivative which has a substituent bonded to the 6-position carbon atom, which used to be difficult to produce by a conventional process for production, and using the same, sulfonylurea herbicides become possible to manufacture on a massive scale.

The invention claimed is:

1. A process for producing a compound represented by the formula (II):

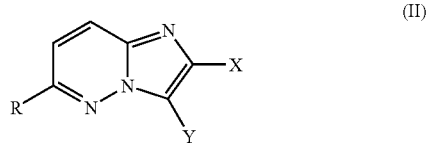

(II)

wherein X represents a halogen group or an optionally halogenated lower alkyl group, Y represents a hydrogen or SO$_2$N═CH—NR$^1$R$^2$ wherein R$^1$ and R$^2$ each represent a lower alkyl group, or R$^1$ and R$^2$ may be combined together with the adjacent nitrogen atom to form a heterocyclic ring, and R represents a lower alkyl group, lower cycloalkyl group which may be substituted with lower alkyl, lower alkenyl group or lower alkynyl group, which comprises reacting an imidazo [1,2-b]pyridazine compound represented by the formula (I):

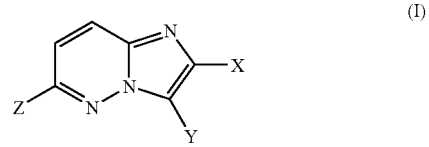

(I)

wherein X and Y are as defined above, and Z represents a halogen atom or OSO$_2$R$^3$ (wherein R$^3$ represents an optionally fluorinated lower alkyl group or phenyl group which may be substituted with lower alkyl), with one or more compounds selected from the organometallic compounds represented by the formula:

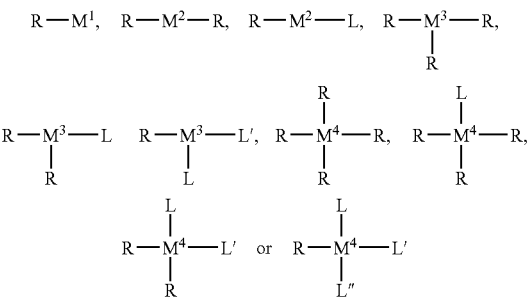

wherein R is as defined above, and M$^1$ represents a univalent metal, M$^2$ represents a divalent metal, M$^3$ represents a trivalent metal and M$^4$ represents a tetravalent metal, and L, L' and L" are the same or different and represent an anion, under the presence of a transition metal catalyst.

2. The process according to claim 1, wherein the metal of the transition metal catalyst is palladium, nickel or iron.

3. The process according to claim 1, wherein the metal of the transition metal catalyst is nickel.

4. The process according to claim 1, wherein the metal of the organometallic compound is magnesium or zinc.

5. The process according to claim 1, wherein R is a lower alkyl group or lower cycloalkyl group which may be substituted with lower alkyl.

6. The process according to claim 1, wherein X and Z are each a chlorine atom.

7. The process according to claim 1, wherein Y is a hydrogen atom and R is a lower alkyl group.

8. The process according to claim 3, wherein the metal of the organometallic compound is magnesium or zinc.

9. The process according to claim 8, wherein the organometallic compound is a lower alkylmagnesium halide or a lower alkylzinc halide.

10. The process according to claim 9, wherein the organometallic compound is a propylmagnesium halide or propylzinc halide and the nickel catalyst is [1,3-bis(diphenylphosphino)propane]nickel(II) dichloride or bis(triphenylphosphine)nickel(II) dichloride.

11. A process for producing a sulfonamide compound represented by the formula (III):

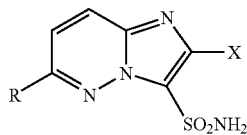

(III)

wherein X represents a halogen atom or an optionally halogenated lower alkyl group and R represents a lower alkyl group, lower cycloalkyl group which may be substituted with lower alkyl, lower alkenyl group or lower alkynyl group, which comprises sulfonating with chlorosulfonic acid a compound represented by the formula (IIa):

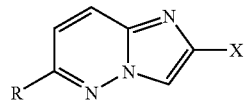

(IIa)

wherein X and R are as defined above, which is obtained by reacting an imidazo[1,2b]pyridazine compound represented by the formula (Ia):

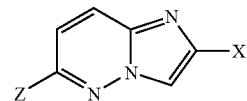

(Ia)

wherein X is as defined above, and Z represents a halogen atom or $OSO_2R^3$ (wherein $R^3$ represents an optionally fluorinated lower alkyl group or phenyl group which may be substituted with lower alkyl), with one or more compounds selected from the organometallic compounds represented by the formula:

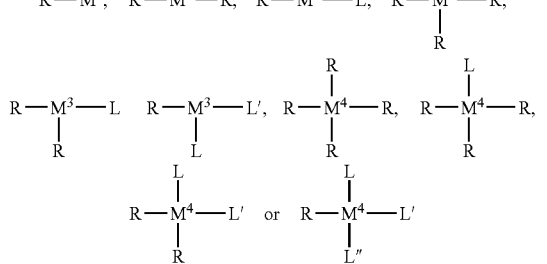

wherein R is as defined above, and $M^1$ represents a univalent metal, $M^2$ represents a divalent metal, $M^3$ represents a trivalent metal and $M^4$ represents a tetravalent metal, and L, L' and L" are the same or different and represent an anion, under the presence of a transition metal catalyst, followed by converting to a sulfonyl chloride with phosphorus oxychloride, then reacting with ammonia.

12. A process for producing a sulfonamide compound represented by the formula (III):

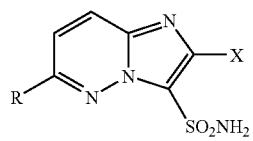

(III)

wherein X represents a halogen atom or an optionally halogenated lower alkyl group and R represents a lower alkyl group, lower cycloalkyl group which may be substituted with lower alkyl, lower alkenyl group or lower alkynyl group, which comprises hydrolyzing under the presence of acid or alkali a compound represented by the formula (IIb):

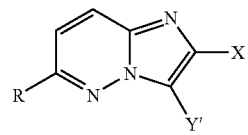

(IIb)

wherein X and R are as defined above and Y' represents $SO_2N=CH-NR^1R^2$ (wherein $R^1$ and $R^2$ each represent a lower alkyl group, or $R^1$ and $R^2$ may be combined together with the adjacent nitrogen atom to form a heterocyclic ring), which is obtained by reacting an imidazo[1,2-b]pyridazine compound represented by the formula (Ib):

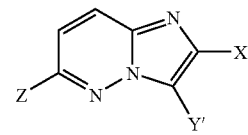

(Ib)

wherein X and Y' are as defined above, and Z represents a halogen atom or $OSO_2R^3$ (wherein $R^3$ represents an optionally fluorinated lower alkyl group or phenyl group which may be substituted with lower alkyl), with one or more compounds selected from the organometallic compounds represented by the formula:

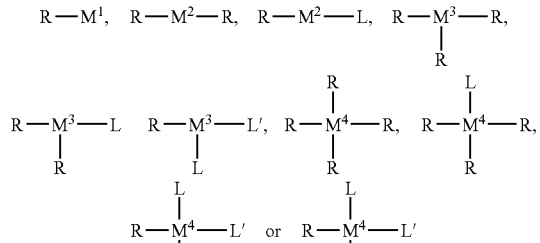

wherein R is as defined above, and $M^1$ represents an univalent metal, $M^2$ represents a divalent metal, $M^3$ represents a trivalent metal and $M^4$ represents a tetravalent metal, and L, L' and L" are the same or different and represent an anion, under the presence of transition metal catalyst.

* * * * *